United States Patent [19]
Stephens

[11] Patent Number: 6,162,647
[45] Date of Patent: Dec. 19, 2000

[54] METHOD FOR REMOVING INTERFERING SUBSTANCES FROM A URINE SAMPLE USING A CHEMICAL OXIDANT

[76] Inventor: James Matthew Stephens, 1332 Michigan, Cincinnati, Ohio 45208

[21] Appl. No.: 08/950,126

[22] Filed: Oct. 14, 1997

[51] Int. Cl.[7] ..................................................... G01N 1/28
[52] U.S. Cl. ............................... 436/175; 436/63; 436/94; 436/106; 436/108; 436/163; 436/901
[58] Field of Search ................................ 436/175, 94, 63, 436/106, 108, 163, 901

[56] References Cited

U.S. PATENT DOCUMENTS

| | | |
|---|---|---|
| 3,966,764 | 6/1976 | Goldstein et al. . |
| 4,315,890 | 2/1982 | Tamers . |
| 5,413,911 | 5/1995 | Adamczyk et al. . |
| 5,464,775 | 11/1995 | Smith . |

FOREIGN PATENT DOCUMENTS

90/12113  10/1990  WIPO .

OTHER PUBLICATIONS

Warner, Clin. Chem. (Winston–Salem NC) (1989), 35(4), 648–51.
Nebinger et al., Lab. Rob. Autom. (1991), 3(6), pp. 237–239.
Schwarzoff et al., J. Anal. Toxicol. (1993), 17(1), 14–17.
Armbruster et al., Clin. Chem. (Washington, DC) (1995), 41(1), 92–8.

*Primary Examiner*—Jan Ludlow
*Attorney, Agent, or Firm*—Charles Hartman

[57] ABSTRACT

Urine samples are made free of potentially interfering substances, such as alkaloids or pharmaceuticals, by contacting the urine sample with an amount of a chemical oxidizing agent, while retaining the physical indicia characteristic of urine to allow the sample to be further tested.

8 Claims, No Drawings

METHOD FOR REMOVING INTERFERING SUBSTANCES FROM A URINE SAMPLE USING A CHEMICAL OXIDANT

BACKGROUND OF THE INVENTION

1. Field of the Invention

This invention relates to urinalysis and methods to make urinalysis more accurate, specifically this invention relates to methods to remove interfering substances from urine.

2. State of the Art

The kidneys remove unwanted substances circulating in the blood producing urine, which is excreted from the body. Consequently, diverse waste substances and other substances unwanted by the body find their way into urine for subsequent removal from the body. Urinalysis is the testing of the composition and amounts of waste substances in urine, and provides a tremendously powerful diagnostic tool for the medical profession. However, some of these unwanted substances can hide existing medical conditions, and some others can masquerade as non-existent medical conditions, undermining the usefulness of urinalysis as a medical diagnostic tool. Some of the unwanted substances that find their way into a urine sample are drugs and drug metabolites, given either as medicaments for conditions such as control of pain or nausea caused by chemotherapy, or voluntarily abused by the urine donor.

Recently, various immunoassays and other kinds of tests have been developed turning urinalysis into a powerful diagnostic tool. For example, quantities of drugs of abuse and other indicia of disease or bodily state can easily be detected by urinalysis. Some pharmaceuticals or other chemicals that might have been ingested disturb the sensitive tests making the actual state of the body difficult or impossible to determine. Among the substances that can be detected in urine, and used to diagnose medical conditions in the patient giving the sample, are insulin levels, para-aminohippuric acid, phenol sulfonphthalein, phosphate, arylsulfatase-A, lysosome, urine amylase, total urine estrogens, specific estrogens, progestins, aldosterone, catecholamines, 5-hydroxyindoleacetic acid, cortisol, homo-vanillic acid, human chorionic gonadotrophin, creatine, urea, uric acid, bilirubin, hemoglobin, hydroxyproline, melanin, porphorins, total protein, acid mucopolysaccharide, copper, glucose oxidase and urine ketone. Removal of the potential masking components of urine can help make the various immunoassays or assays by other techniques, such as isolation followed by gas or liquid chromatography followed by mass spectrometry, more accurate.

One compound that may be found in urine results from the chemotherapy to relieve the distressing symptoms of cancer chemotherapy or voluntary ingestion from abuse is tetrahydrocannabinol. A method for detecting this compound is described in U.S. Pat. No. 5,036,013, issued to ElSohly et al., where various deuterated cannabinoids are synthesized to help determine the quantitative amount of tetrahydrocannabinol in a urine sample. Various methods are described therein. One method in particular involves spiking a urine sample with deuterated tetrahydrocannabinol and analyzing the resultant sample with gas chromatography/mass spectrum.

Another example of the problems created by interfering chemicals in urine is exemplified by the case of ibuprophan. Ibuprophan is a prostaglandin synthetase inhibitor that may be taken in large doses to relive pain and inflammation characteristic of arthritis. When a patient taking these massive doses is subjected to urinalysis, it may mask other drugs of abuse, or may be mistaken for tetrahydrocannabinol. Such a misidentification of a drug of abuse can have devastating personal consequences for the tested patient. Therefore, removal of the masking compound before the test would improve the reliability of the test, and prevent possible liability to those requesting the test.

SUMMARY OF THE INVENTION

This invention provides a method to make urine samples obtained by conventional methods free of potentially interfering substances, such as tetrahydrocannabinol, by contacting the urine sample with a solution containing an amount of a chemical oxidizing agent. The chemical oxidizing agent has a concentration of greater than about 10%. The urine samples still retain physical indicia characteristic of urine allowing the sample to be further tested.

In one aspect of this invention, a urine sample is collected, then, before any testing, an unwanted substance is removed from urine samples by contacting the urine sample with an amount of a chemical oxidizing agent sufficient to oxidize at least 20% of the unwanted substance in a volume of urine while leaving the various physical indicia characteristic of urine unaffected.

In another aspect of this invention, a urine sample is collected, then, before any testing, an unwanted substance is removed from urine samples by contacting the urine sample with an amount of a chemical oxidizing agent comprising a combination of a chemical oxidizing agent and at least one acid sufficient to oxidize at least 20% of the unwanted substance in a volume of urine while leaving the various physical indicia characteristic of urine unaffected, wherein at the hydrolysing acids is a mineral acid selected from the group consisting of hydrochloric, nitric, sulfuric, phosphoric, perchloric, hydroiodic, hydrobromic, hydrofluoric.

DETAILED DESCRIPTION OF THE PREFERRED EMBODIMENT

In the process of this invention, a patient being tested provides a urine sample for subsequent urinalysis. It is collected by any of a variety of well known conventional methods. The physician or other technician can then analyze the sample immediately or send it off to a specialized laboratory for subsequent analysis. The process of this invention requires that before any subsequent testing be done to the sample, an amount of hydrolysing acid be added to the urine sample.

The urine sample is contacted with an amount of an chemical oxidizing agent sufficient to oxidize at least 20%, preferably at least 30%, and most preferably at least 50%, of the unwanted substance in a volume of urine. It is preferred that the chemical oxidizing agent is in the form of an aqueous solution. The chemical oxidizing agent leaves the various physical indicia characteristic of urine substantially unaffected and the trace substances that are not to be tested for are removed while leaving a urine sample that can be otherwise tested as normal. The means of contact can be mixing an aqueous solution of the hydrolysing acid with the urine sample before subsequent testing.

The solution of oxidizing agent used in this invention can contain any agent normally used to oxidize organic components. Preferred agents include hydrogen peroxide, benzoyl peroxide, chromium trioxide, sodium permanganate, and potassium permanganate. Hydrogen peroxide is used as an aqueous solution having between 10% and 75% active ingredient. It is preferred to use hydrogen peroxide having a concentration of between about 40% and 60%, and commercially available 50% solution can be used. The oxidizing salts are preferably prepared as saturated solutions in deionized water, although more dilute solutions can be used. The aqueous solution of oxidizing agent is then added to the preparation of the invention. It is preferred to use noncolored agents, as the urine may be subjected to various colorometic tests.

In a preferred embodiment, a hydrolysing acid is included as an ingredient of the oxidizing solation. The hydrolysing acid of the invention is preferably a mineral acid or an organic acid. Preferred mineral acids include, but are not limited to, the group consisting of hydrochloric, nitric, sulfuric, sodium bisulfate, phosphoric, polyphosphoric, monosodium phosphate, disodium phosphate, perchloric, hydroiodic, hydrobromic, and hydrofluoric. Organic acids may be selected from the group consisting of organic acids having the general formula of R—(COOX)$_y$ where R is any lower alkyl or aryl radical having 1 to 6 carbon atoms, X may be the same or different and may be hydrogen or alkali or alkaline earth metals, provided that at least one X is a hydrogen, and y is any number between 1 and 3. Preferred alkali and alkaline earth metals include lithium, sodium, potassium, beryllium, calcium, and magnesium. X may be chosen from the group consisting of zinc and manganese as well. Preferred organic acids include, but are not limited to, acetic, formic, oxalic, mono-sodium oxalic, propionic, malic, mono-potassium malic, butyric, succinic, citric, tartaric, benzoic, phthalic, mono-potassium phthalic, and flouroacetic acids. Organic acids having four or fewer carbon atoms having one, two or three carboxyl groups are especially preferred for this invention. Although it is not necessary, it is preferred that the acid be monoprotic, that is, that it have only one acidic hydrogen atom. In general, any water soluble acid would work, but for purposes of this invention it is preferred that the anion left by the acid be an anion normally found in urine. Therefore, the greatly preferred mineral acid for use in this invention is hydrochloric acid and the preferred organic acids are tannic acid, citric acid, and acetic acid. The concentration of the hydrolysing acid to be added to the urine sample acid has a concentration of greater than 1 Normal, more preferably greater than 3 Normal and most preferably greater than 3.5 Normal. The ph of the hydrolysing acid solution will be between about 2 and 0.5, preferably between about 1 and 0.75.

The hydrolysing acid solution used in this invention can a mixture of a primary, or first, acid and a secondary, or second, acid. The first acid can be one of the acids listed above and the second acid can be one acid or a combination of more than one acid in solution. For example, the second acid may be one or more acids selected from the group consisting of hydrochloric, nitric, sulfuric, sodium bisulfate, phosphoric, monosodium phosphorate, disodium phosphorate, perchloric, hydroiodic, hydrobromic, hydrofluoric, or an organic acid selected from the group consisting of organic acids having the general formula of R—(COOX)$_y$ where R is any lower alkyl or aryl radical having 1 to 6 carbon atoms, X may be the same or different and is hydrogen or alkali or alkaline earth metals, provided that at least one X is hydrogen, and y is any number between 1 and 3. Preferred alkali and alkaline earth metals include lithium, sodium, potassium, beryllium, calcium, and magnesium. Preferred organic acids include acetic, formic, oxalic, monosodium oxalic, propionic, malic, monopotassium malic acid, butyric, succinic, citric, tartaric, benzoic, phthalic, potassium hydrophthalic acid, and flouroacetic acids. Organic acids having four or fewer carbon atoms having one or two carboxyl groups are preferred for this invention. The concentration of the acidic hydrogens in any combination of acids to be added to the urine sample has a effective concentration of greater than 1 Normal, more preferably greater than 3 Normal and most preferably greater than 3.5 Normal. Effective concentration means that a solution of a combination of acids is 1N if 1 liter of 1N sodium hydroxide solution exactly neutralizes 1 liter of the acid combination. The pH of the combination acid solution will be between about 2 and 0.5, preferably between about 1 and 0.75.

One particularly preferred acid for use in this invention is 20° Baumé hydrochloric acid that has been cut to between 10 and 30 volume percent, more preferably, between about 15 and 25 volume percent, by water.

Preferably, the acid added to a urine sample does not harm other indicia present in the urine. Such indicia is used for diagnosis of disease, and bodily state, such as pregnancy. Such indicia include, pH, saccharide content, red blood cell count, nitrogen content, albumin content, protein content, immunoassayable proteins, and total solids content. Immunoassayable proteins include HCG, and other proteins used to diagnose congenital diseases, cancer, and other abnormalities. It is preferred that the method of the invention leaves the indicia required for successful testing of insulin levels, para-aminohippuric acid, phenol sulfonphthalein, phosphate, arylsulfatase-A, lysosome, urine amylase, total urine estrogens, specific estrogens, progestins, aldosterone, catecholamines, 5-hydroxyindoleacetic acid, cortisol, homovanillic acid, human chorionic gonadotrophin, creatine, urea, uric acid, bilirubin, hemoglobin, hydroxyproline, melanin, porphorins, total protein, acid mucopolysaccharide, copper, glucose oxidase and urine ketone substantially unaffected.

Preferably, adding the hydrolysing solution of this invention removes at least 25% of the interfering substance, preferably at least 33%, and most preferably at least 50%, when measured on a wt/volume basis.

In general, the unwanted substances removed by this invention are natural products or pharmaceuticals. Preferably the substances are alkaloids or other naturally occurring substances. In another embodiment, the unwanted substances are selected from the group consisting of testosterone, estrogen, progesterone, anabolic steroids, ibuprophan, acetaminophen, acetosalicylic acid, benzedrine, 3,4,5-trimethoxy-benzedrine, tetrahydrocannabinol, cocaine, morphine, codeine, nicotine, ethyl alcohol, and acetaldehyde. The method of this invention can remove a substantial amount of the unwanted substances while not interfering with the other indicia for the various tests enumerated above.

EXAMPLES

The invention can be better understood by reference to the following illustrative Examples of the preferred embodiment of the invention, which Examples are meant to illustrate the invention and not to limit the scope of the invention in any way.

Example 1

In this example, a urine additive solution is made.

30 mls of commercially obtained aqueous 50% hydrogen peroxide is added to enough deionized water to make up 100 mls of solution. This solution is used in the tests and preparations of the following Examples.

Similarly, a chemical oxidizing agent solution can be made with aqueous benzoyl peroxide, saturated aqueous chromium trioxide, saturated aqueous sodium permanganate, and saturated aqueous potassium permanganate solutions.

Example 2

In this Example, various additives are added to the solution of Example 1 to create solutions that can remove interfering solutions.

10 ml of commercially obtained 20° Baumé hydrochloric acid is added to 100 mls of the solution of Example 1 making an oxidizing-hydrolysing solution.

Similarly, new oxidizing-hydrolysing solutions are made adding acetic, nitric, sulfuric, sodium bisulfate, phosphoric, monosodium phosphorate, disodium phosphorate, perchloric, hydroiodic, hydrobromic, hydrofluoric acetic, formic, oxalic, sodium hydrooxalic acid, propionic, malic, potassium hydromalic acid, butyric, succinic, citric, tartaric, benzoic, phthalic, potassium hydrophthalic acid, and flouroacetic acids to the solution of Example 1.

Example 3

In this Example, various additives are placed in the solution of Example 2.

In another preferred embodiment, 10 ml of potassium hydrophthalic acid is added to the solution of Example 2, producing an oxidizing-diacidic hydrolysing solution useful for the process of this invention.

Similarly, new solutions are made adding nitric, sulfuric, sodium bisulfate, phosphoric, monosodium phosphorate, disodium phosphorate, perchloric, hydroiodic, hydrobromic, hydrofluoric acetic, formic, oxalic, sodium hydrooxalic acid, propionic, malic, potassium hydromalic acid, butyric, succinic, citric, tartaric, benzoic, phthalic, and flouroacetic acids to the solution of Example 2.

Example 4

In this Example, the solution of Example 1 is used to remove unwanted interfering substances from a urine sample.

Urine samples are collected in conventional ways. The samples are divided into two equal aliquots. The control is analyzed in the usual way without any further preparation. 10 mls of the oxidizing-hydrolysing solution of Example 2 are added to the second aliquot. The samples are worked up by first separating the sample using gas chromatography, and subsequent analysis by mass spectroscopy. Typically expected results, tabulated by aliquot are presented in Table 1.

TABLE 1

| ALIQUOT # | THC ng/ml | % REDUCTION | pH | SPECIFIC GRAVITY |
|---|---|---|---|---|
| 1a | 1225 | | 5 | 1.03 |
| 1b | 735 | 40% | 5 | 1.03 |
| 2a | 75 | | 5 | 1.01 |
| 2b | 48 | 35% | 5 | 1.01 |
| 3a | 50 | | 6.0 | 1.01 |
| 3b | 35 | 30% | 6.0 | 1.01 | where "a" and "b" in the aliquot number refer to the two aliquots produced from the same original sample sent to the testing laboratory.

Table 1 indicate that the oxidizing-hydrolysing solution may reduce the presence of tetrahydrocannabinol by about an average of 35% regardless of the initial concentration of the amount of interfering substance. The pH of the samples, one of the normal indicia tested in standard urinalysis, remains substantially unchanged after the use of the oxidizing-hydrolysing solution, as does the specific gravity.

Similar results are observed when the hydrolysing acid from Examples 1 and 3 are substituted for the oxidizing-hydrolysing solution of Example 2 in the test protocol outlined above.

Although this invention has been primarily described in terms of specific examples and embodiments thereof, it is evident that the foregoing description will suggest many alternatives, modifications, and variations to those of ordinary skill in the art. Accordingly, the appended claims are intended to embrace as being within the spirit and scope of invention, all such alternatives, modifications, and variations.

I claim:

1. A method to remove detectable amounts of an unwanted substance from a human urine sample comprising:

obtaining a human urine sample having detectable amounts of an unwanted substance selected from the group consisting of testosterone, estrogen, progesterone, anabolic steroids, ibuprofen, acetaminophen, acetylsalicylic acid, amphetamine, tetrahydrocannabinol, cocaine, morphine, codeine, nicotine, ethyl alcohol, and acetaldehyde;

contacting the human urine sample with an amount of chromium trioxide, sufficient to oxidize at least 25% of the unwanted substance in a volume of urine while leaving at least one physical indicia selected from the group consisting of pH, nitrogen content, saccharide content, red blood cell count, and total solids content characteristic of the urine sample unaffected, while leaving the color of the resulting solution substantially unaffected.

2. The method of claim 1 wherein said at least one of the physical indicia characteristic of urine is pH.

3. The method of claim 1 wherein said at least one of the physical indicia characteristic of urine is saccharide content.

4. The method of claim 1 wherein said at least one of the physical indicia characteristic of urine is red blood cell count.

5. The method of claim 1 wherein said at least one of the physical indicia characteristic of urine is nitrogen content.

6. The method of claim 1 wherein said at least one of the physical indicia characteristic of urine is total solids content.

7. The method of claim 1 wherein the amount of substance removed is at least 30%.

8. The method of claim 7 wherein the amount of substance removed is at least 50%.

* * * * *